United States Patent
Reimer et al.

(10) Patent No.: US 9,377,441 B2
(45) Date of Patent: Jun. 28, 2016

(54) REDUCTION OF AERATION INTERFERENCE IN AN ULTRASONIC FLUID SENSING SYSTEM

(71) Applicant: SSI Technologies, Inc., Janesville, WI (US)

(72) Inventors: Lawrence B. Reimer, Georgetown, SC (US); Gregory P. Murphy, Janesville, WI (US); David T. Schlenke, Janesville, WI (US)

(73) Assignee: SSI TECHNOLOGIES, INC., Janesville, WI (US)

( * ) Notice: Subject to any disclaimer, the term of this patent is extended or adjusted under 35 U.S.C. 154(b) by 222 days.

(21) Appl. No.: 14/044,444

(22) Filed: Oct. 2, 2013

(65) Prior Publication Data

US 2015/0089996 A1    Apr. 2, 2015

(51) Int. Cl.
*G01N 29/02* (2006.01)
*G01N 29/024* (2006.01)
*G01N 29/32* (2006.01)
*G01N 33/28* (2006.01)

(52) U.S. Cl.
CPC .............. *G01N 29/02* (2013.01); *G01N 29/024* (2013.01); *G01N 29/32* (2013.01); *G01N 33/2835* (2013.01); *G01N 2291/0226* (2013.01); *G01N 2291/0228* (2013.01)

(58) Field of Classification Search
CPC ..... G01N 29/02; G01N 29/024; G01N 29/32; G01N 33/2835; G01N 2291/0226; G01N 2291/0228

USPC .............. 73/19.03, 19.1, 61.76, 61.79, 64.53, 73/32 A
See application file for complete search history.

(56) References Cited

U.S. PATENT DOCUMENTS

| 4,079,623 | A  | 3/1978  | Erwin, Jr. |
|-----------|----|---------|------------|
| 7,118,206 | B1 | 10/2006 | Stockwell et al. |
| 2003/0181794 | A1 | 9/2003 | Rini et al. |
| 2011/0166802 | A1 | 7/2011 | Kong et al. |
| 2011/0228641 | A1 | 9/2011 | Niemann |

FOREIGN PATENT DOCUMENTS

| JP | 63-250559 A | 10/1988 |
| JP | 2005299441  | 10/2005 |

OTHER PUBLICATIONS

International Search Report and Written Opinion of the International Searching Authority for Application No. PCT/US14/56520 dated Dec. 15, 2014 (9 pages).

*Primary Examiner* — Daniel S Larkin
(74) *Attorney, Agent, or Firm* — Michael Best & Friedrich LLP (57) ABSTRACT

A fluid sensor for sensing at least one characteristic of a fluid. The fluid sensor includes a sensing area, a sensing element and a mesh. The sensing element is configured to sense a characteristic of fluid located within the sensing area. The mesh is positioned around the sensing area. The mesh is configured to allow a liquid portion of the fluid to enter and exit the sensing area, and substantially prohibit a gas portion of the fluid to enter the channel.

15 Claims, 9 Drawing Sheets

REDUCTION OF AERATION INTERFERENCE IN AN ULTRASONIC FLUID SENSING SYSTEM

BACKGROUND

The present invention relates to systems for sensing a fluid. More particularly, embodiments of the invention relate to mechanisms and techniques for reducing interference in measurements caused by air bubbles (e.g., a gas trapped in a liquid) in fluid level and concentration sensors.

Fluid level and fluid concentration sensing is important in a number of vehicle applications including, for example, the sensing of Diesel Exhaust Fluid (DEF) used in a selective catalytic reduction diesel emission-control system. Selective catalytic reduction (SCR) is a method of converting diesel oxides of nitrogen (NOx) emissions, by catalytic reaction, into diatomic benign nitrogen gas ($N_2$) and water ($H_2O$). DEF is used in the process. In clean diesel engines, an SCR system delivers near-zero emissions of NOx.

DEF is a mixture of purified water and urea. In a typical SCR system, DEF is stored in a tank of a vehicle and is injected via one or more injectors into the exhaust at a ratio of about 1:50 to the diesel fuel being burned. The injected urea (in the form of a mist) mixes with the exhaust and breaks down NOx in the exhaust into nitrogen, water, and carbon dioxide.

When contaminants such as diesel fuel, water, and ethylene glycol, mix with the DEF, the ability of the DEF to reduce the NOx in the exhaust is diminished. Contaminated DEF may also cause damage to the NOx reluctant system. It is also important that a sufficient amount of DEF be available for use in the SCR system. In or near the tank, one or more sensors are used to sense certain characteristics of the DEF. The sensors may include, but are not limited to: a level sensor for determining a quantity of DEF in the tank; a concentration sensor for determine the quality of DEF in the tank; and a temperature sensor. Fluid level is representative of the amount or quantity of fluid and concentration is one characteristic that is representative of the quality of the fluid.

SUMMARY

It has been recently observed that DEF fluid in an SCR system can become aerated (i.e., mixed with air in such a way that bubbles of air are entrained in the fluid). Aeration can occur, for example, during rapid filling or refilling of a tank or reservoir for DEF fluid. Aeration can also occur during severe vibration, fluid sloshing violently within the tank, or may be present in the return flow of the DEF fluid if a pump of the SCR system ingests air. Similar aeration can occur in other fluids as well, including but not limited to, gasoline fuel, diesel fuel, engine oil, hydraulic fluid, and transmission fluid.

Generally, accurate fluid measurements require a homogeneous fluid from which to measure the speed of sound. When the fluid is aerated the path of the ultrasonic sound waves are dispersed by the presence of air bubbles. This interference of the sound waves causes a loss in the reflected echo (i.e., no speed of sound measurement) and thus a loss of accurate fluid measurements.

Accordingly, in one embodiment, the invention provides a filter, and more specifically, a fluid sensor including a filter. The filter blocks, or inhibits, air bubbles from entering a sensing area of the fluid sensor. The sensing area contains the fluid to be sensed. The fluid is sensed by generating an ultrasonic pulse wave through the fluid contained within the sensing area. The time of flight of the ultrasonic pulse wave travelling the distance of the sensing area and returning to the output point is measured. If air bubbles are embedded within the fluid, the bubbles disperse the ultrasonic signal resulting in the fluid sensor not receiving the echo reflection, and thus no accurate time of flight measurement. These changes cause erratic measurement results or result in no measurement results.

In another embodiment, the invention provides a fluid sensor for sensing at least one characteristic of a fluid. The fluid sensor includes a sensing area; a sensing element configured to sense a characteristic of fluid located within the sensing area; and a mesh positioned around the sensing area. The mesh is configured to allow a liquid portion of the fluid to enter and exit the sensing area, and substantially prohibit a gas portion of the fluid to enter the channel while providing an exit, or exhaust, for trapped gas to escape.

In another embodiment the invention provides a method of preventing gas bubbles in a sensing system for sensing a fluid contained in a tank, where the sensing system includes a sensing area and a sensor. The method includes coupling a mesh to the sensing system, wherein the mesh covers the sensing area; allowing a liquid portion of the fluid to enter and exit the sensing area through the mesh; prohibiting a gas portion of the fluid entering the sensing area; and sensing a characteristic of the fluid contained within the sensing area.

It should be observed that the invention is applicable to a variety of fluids, including but not limited to, gasoline fuel, diesel fuel, engine oil, hydraulic fluid, and transmission fluid, all of which are known to foam during sloshing and heavy vibration conditions.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Although the invention described herein can be applied to, or used in conjunction with a variety of fluids, fuels and oils (e.g., gasoline fuel, diesel fuel, engine oil, hydraulic fluid, transmission fluid, etc.), embodiments of the invention described herein are described with respect to DEF for use in an SCR system.

Figure 1:
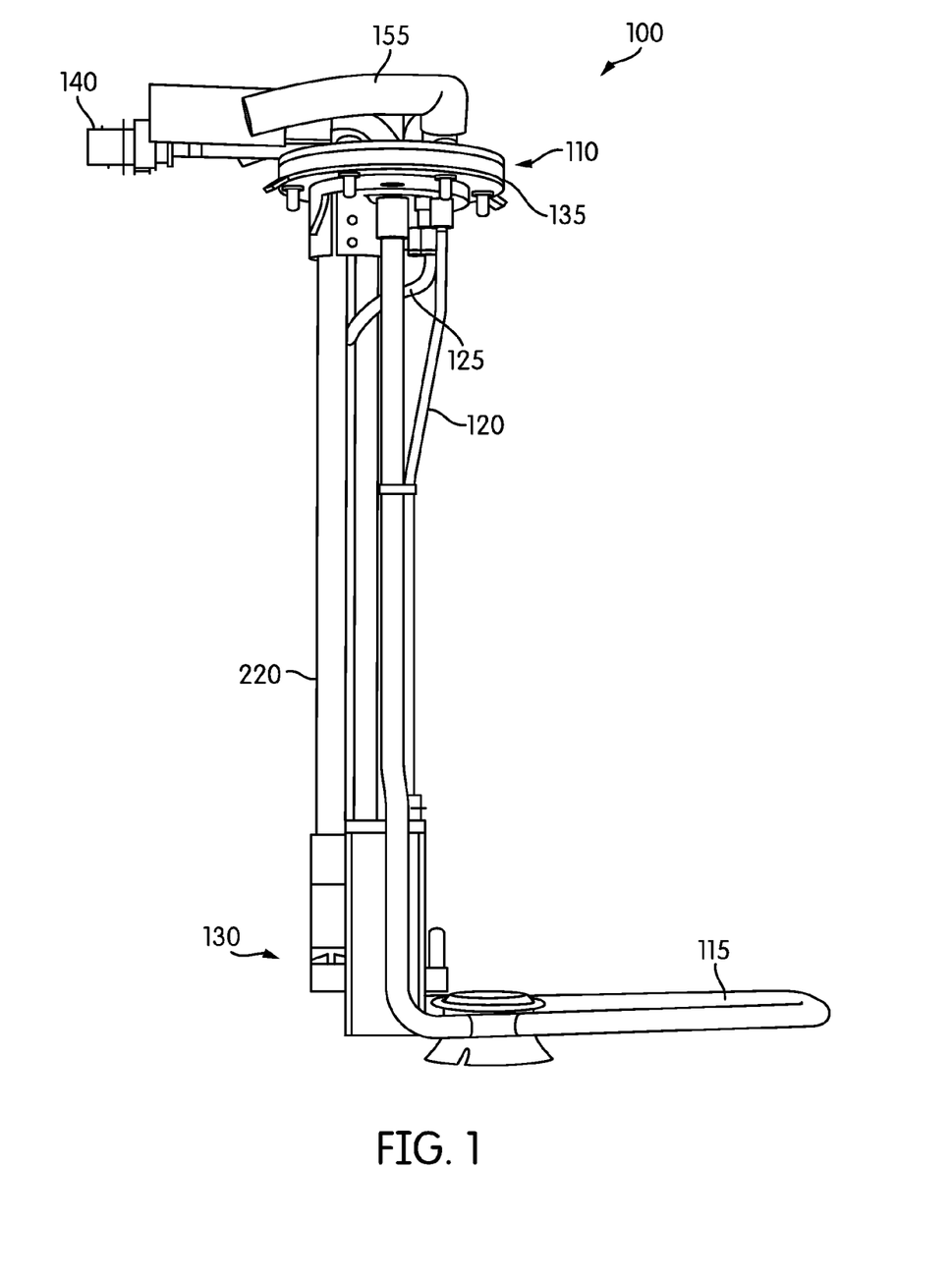
FIG. 1 is a side view of an apparatus for sensing and transporting a fluid.
Figure 2:
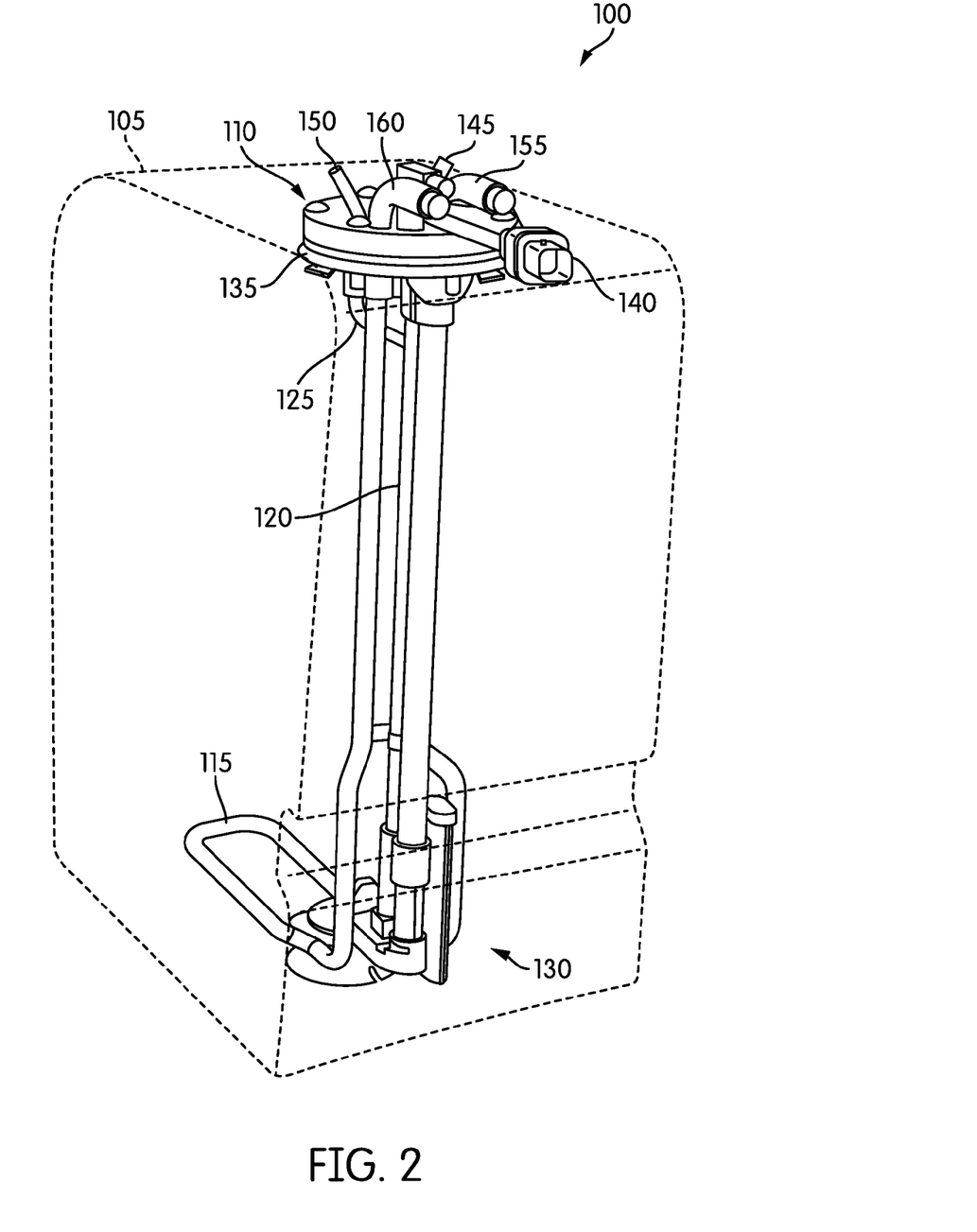
FIG. 2 is a perspective view of the apparatus of FIG. 1.

FIGS. 1 and 2 illustrate an apparatus 100 for sensing and heating a fluid within a tank 105. As noted, in some embodiments, the fluid is DEF (e.g., a urea solution, liquid urea, urea, or Adblue™ fluid). The fluid has a liquid portion and a gas portion. In some embodiments, the gas portion represents bubbles of air, or another gas, present in the fluid.

The apparatus 100 includes a header 110, a heater loop 115, a pickup line 120, a return line 125, and a sensor system 130. The header 110 encloses the fluid inside the tank 105. In some embodiments, a gasket 135 seals the header 110 to the tank 105. The header 110 includes a plurality of fittings and an electrical connector 140. In some embodiments, the plurality of fittings include a pickup fitting 145, a return fitting 150, a coolant input fitting 155, and a coolant output fitting 160. The plurality of fittings provides various paths for fluid to be transported or directed into, out of, and through the tank 105. The electrical connector 140 provides an electrical connection from the sensor system 130 to an external computer system (e.g., a vehicle's data bus).

Figure 3:
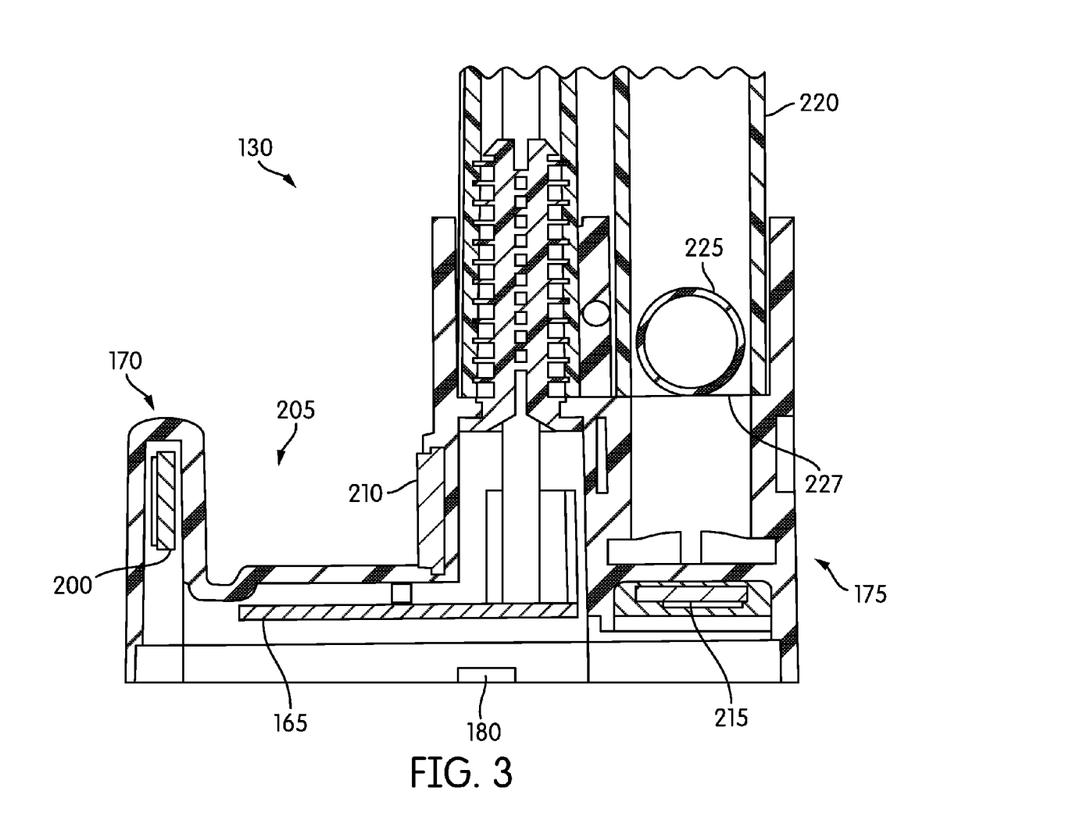
FIG. 3 is a sectional view of a sensing system used in the apparatus of FIGS. 1 and 2.
Figure 4:
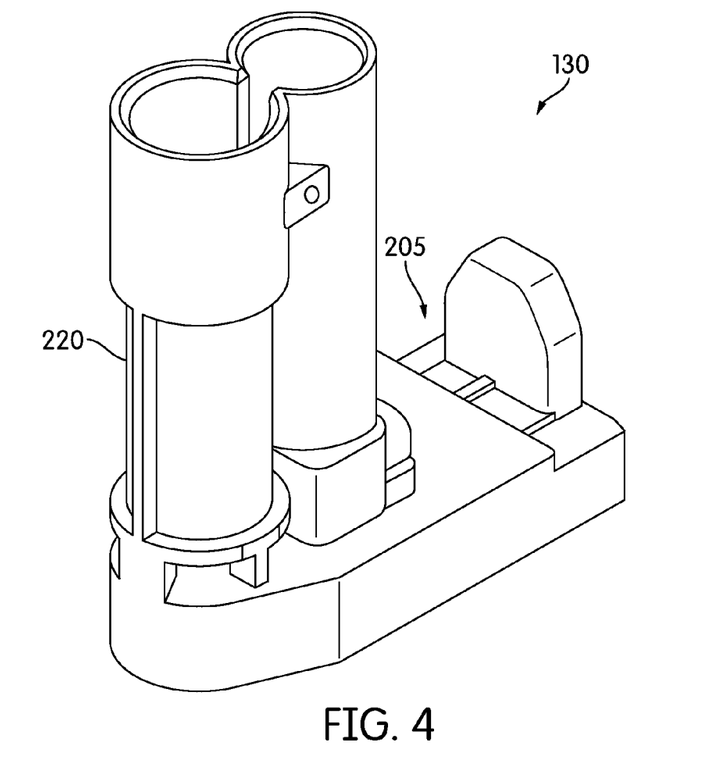
FIG. 4 is a perspective view of the sensing system of FIG. 3.

FIGS. 3 and 4 illustrate the sensor system 130. FIG. 3 illustrates a sectional view of the sensor system 130. The sensor system 130 includes a printed circuit board (PCB) 165 and a plurality of sensors (i.e., sensing elements). In the illustrated embodiment, the plurality of sensors includes a concentration sensor 170, a level sensor 175, and a temperature sensor 180. In other embodiments, the sensor system 130 may include more or less sensors than shown in the illustrated embodiment. Each of the plurality of sensors is electrically coupled to the PCB 165. In some embodiments, the PCB 165 includes a sensor control system, which, among other things, provides power to the plurality of sensors; analyzes data from the plurality of sensors; and outputs the analyzed data to other components such as an external computer.

The concentration sensor 170 determines a concentration, and thus a quality, of the fluid within the tank 105. The concentration sensor 170 includes a concentration piezoelectric ultrasonic transducer (PZT) 200, a measurement channel 205, and a concentration reflector 210. The concentration PZT 200 is a sensing element configured to act as both a transmitter and receiver. The measurement channel 205 acts as a sensing area for containing a fluid to be sensed. In operation, the concentration PZT 200 generates an acoustic wave signal, which propagates through the fluid, contained within the measurement channel 205, toward the concentration reflector 210. The acoustic wave signal reflects off of the concentration reflector 210 and travels back toward the concentration PZT 200. The concentration time-of-flight (ToF) of the acoustic wave signal is output to the sensor control system of the sensor system 130. Although shown in the illustrated embodiment, other embodiments of the apparatus 100 do not include a concentration sensor 170.

The level sensor 175 determines a level, and thus a quantity, of the fluid within the tank 105. In the illustrated embodiment, the level sensor 175 includes a level PZT 215 and a level sensing tube 220 (e.g., a level focus tube). The level PZT 215 is a sensing element configured to act as both a transmitter and receiver. The level sensing tube 220 acts as a sensing area for containing a fluid to be sensed. Some embodiments also include a float. In the particular embodiment illustrated, the level sensor 175 includes a float 225 located within the level sensing tube 220. Although illustrated as a sphere in FIG. 3, the float 225 may be another shape, including but not limited to, a cylinder. The float 225 floats on the surface of the DEF solution contained within the tank 105. The level PZT 215 generates an acoustic wave signal, which propagates through the fluid contained within the level sensing tube 220. The acoustic wave signal propagates toward the float 225. The acoustic wave signal reflects off of the float 225, contained within the level sensing tube 220, and travels back toward the level PZT 215. In one embodiment not including the float 225, the level PZT 215 generates an acoustic wave signal, which propagates through the fluid, contained within the level sensing tube 220, toward a surface 227 of the fluid. The acoustic wave signal reflects off of the surface of the fluid and travels back toward the level PZT 215. The ToF of the acoustic wave signal is output to the sensor control system.

The temperature sensor 180 determines a temperature of the fluid within the tank. In one embodiment the temperature sensor 180 is a thermocouple. In another embodiment, the temperature sensor 180 is a thermistor. In yet another embodiment, the temperature sensor 180 is a resistance temperature sensor. In yet another embodiment, the temperature sensor 180 is an infrared temperature sensor. The temperature sensor 180 outputs the sensed temperature to the sensor control system. In some embodiments, the level sensor 175 and the temperature sensor 180 are combined into a combination sensor capable of sensing both a level and a temperature. In some embodiments, the concentration sensor 170 and the temperature sensor 180 are combined into a combination sensor capable of sensing both a concentration and a temperature of the fluid. In other embodiments, the level sensor 175, the temperature sensor 180, and the concentration sensor 170 are combined into a combination sensor capable of sensing all three metrics.

Figure 5:
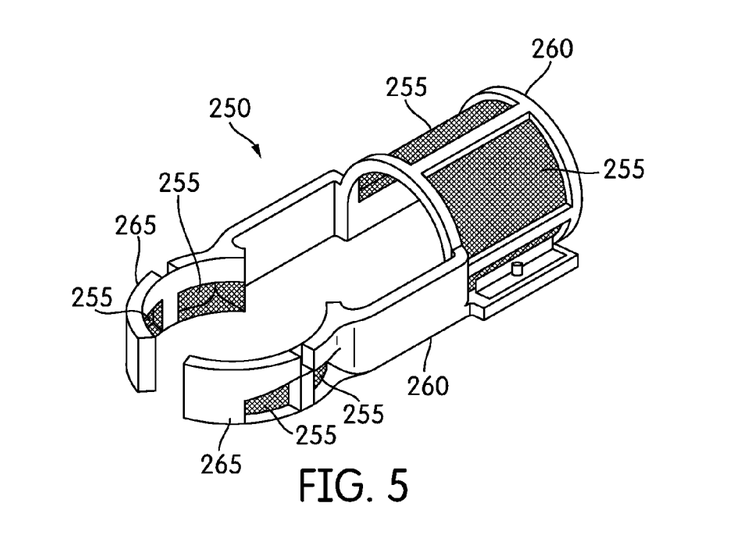
FIG. 5 is a perspective view of one embodiment of a filter shroud.

FIG. 5 illustrates a filter, or filter shroud, 250 for prohibiting, or inhibiting, the flow of gas, such as but not limited to, gas bubbles (i.e., gas trapped in a liquid). In some embodiments, the filter 250 includes mesh, or one or more mesh screens, 255 and a frame 260. In other embodiments, the filter 250 includes only the mesh screens 255. In some embodiments, the mesh screens 255 are a fine mesh material. In some embodiments, the mesh screens 255 are a synthetic polymer (e.g., nylon, polyethylene, polypropylene, etc.). In other embodiments, the mesh screens 255 are a metallic material.

The frame 260 couples the filter 250 to the sensor system 130. The frame 260 includes one or more arms 265. In some embodiments, the frame 260, and the arms 265, are made of a plastic, or plastic like, material. In the illustrated embodiment, the arms 265 are coupled to a housing of the sensor system 130. In some embodiments, the arms 265 couple to a housing of the level sensing tube 220 of the sensor system 130.

In the certain embodiments of the invention, the corollary to a particle is a gas bubble trapped within the fluid. The mesh screens 255 act to prevent the gas bubbles from entering into a sensing area (e.g., the measurement channel 205, the level sensing tube 220, etc.), while allowing liquid, or a liquid portion to enter the sensing area or sensing areas.

In one embodiment, gas bubbles within the fluid having a size larger than an aperture size of the mesh screens 255 are unable to freely pass through the mesh screens 255. However, a liquid portion of the fluid, can freely pass through the mesh screens 255, as well as gas bubbles which have a diameter smaller than the aperture size of the mesh screens 255. It has been found through empirical testing of a DEF tank system that an aperture size of 100 microns reduces the quantity of gas bubbles within a sensing area sufficiently enough to enable continuous measurements by the concentration sensor 170 and/or the level sensor 175.

Figure 6:
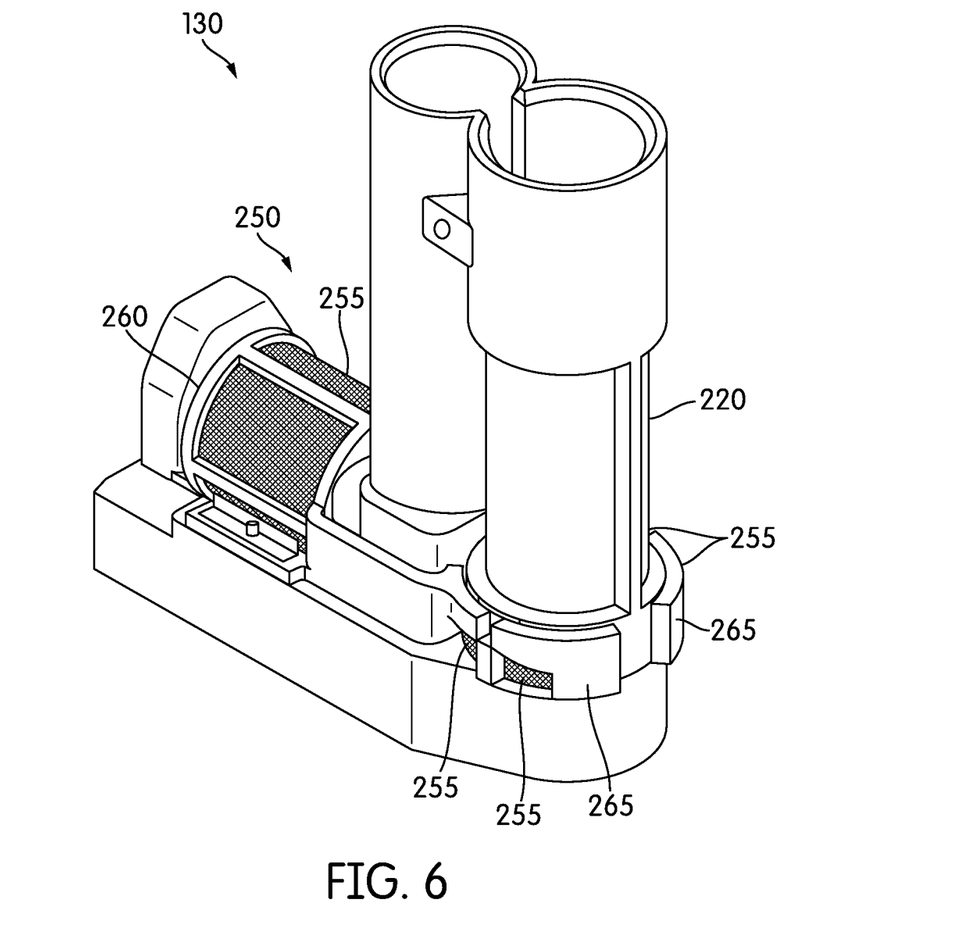
FIG. 6 is a perspective view of the filter shroud of FIG. 5 coupled to the sensing system of FIGS. 3 and 4.
Figure 7:
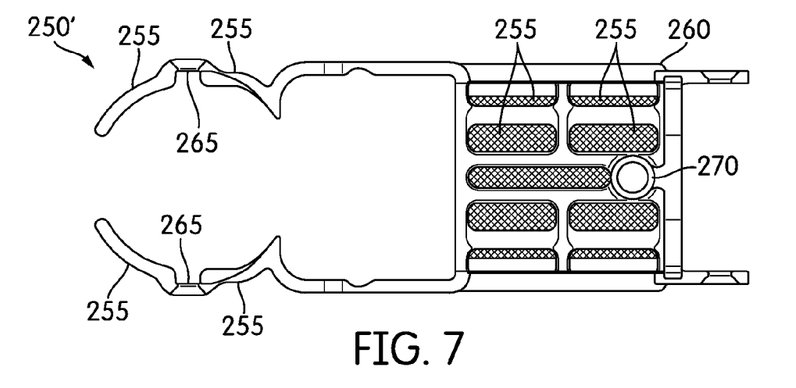
FIG. 7 is a top view of another embodiment of a filter shroud.
Figure 8:
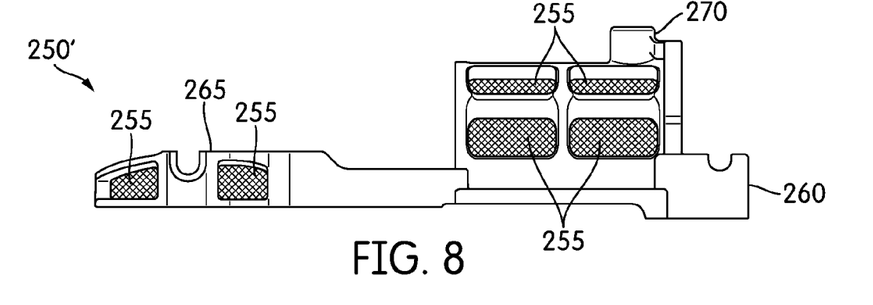
FIG. 8 is a side view of the filter shroud of FIG. 7.
Figure 9:
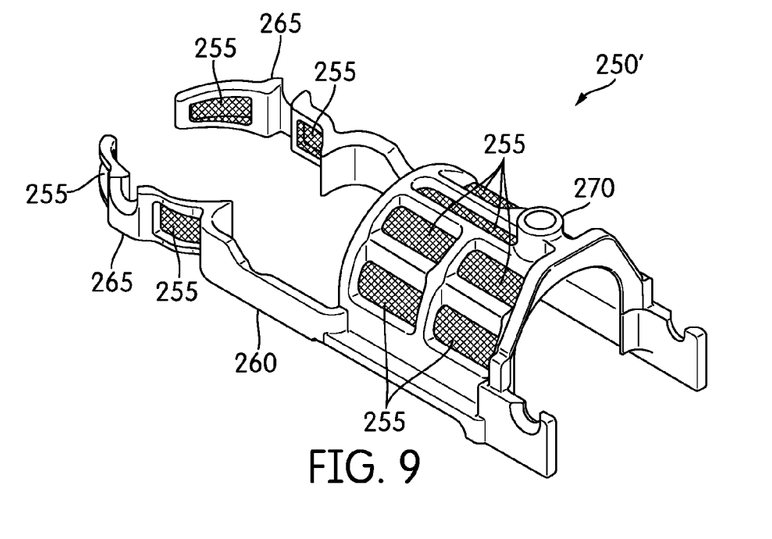
FIG. 9 is a perspective view of the filter shroud of FIGS. 7 and 8.
Figure 10:
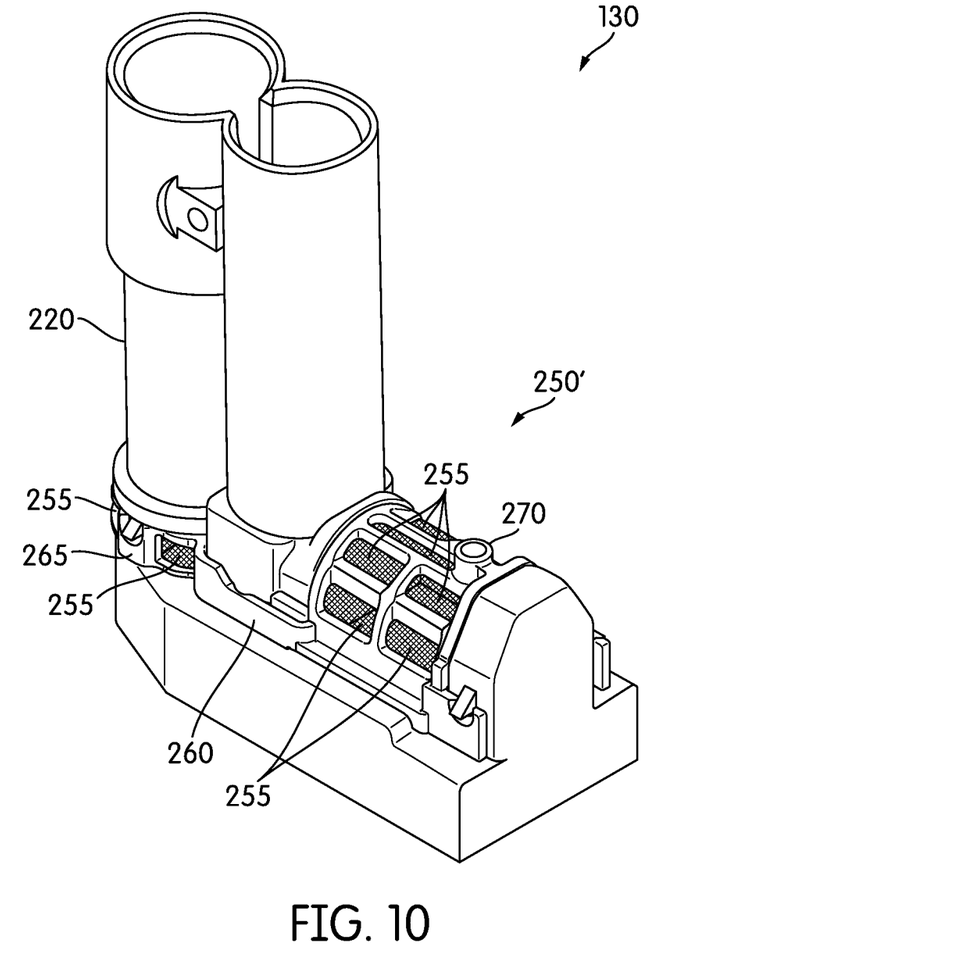
FIG. 10 is a perspective view of the filter shroud of FIGS. 7-9 coupled to the sensing system of FIGS. 3 and 4.

FIG. 6 illustrates the filter 250 coupled to sensor system 130. In the illustrated embodiment, the filter 250 allows liquid, or a liquid portion of the fluid, to pass through the mesh screens 255 into a sensing area (e.g., the measurement channel 205, the level sensing tube 220, etc.), while inhibiting the flow of gas bubbles into the sensing area or sensing areas. In the illustrated embodiment, the mesh screens 255 enclose the measurement channel 205 and one or more inlets of the level sensing tube 220. In the illustrated embodiment, the mesh screen 255 is held in place by the frame 260. The frame 260 is coupled to the housing of the sensor system 130 via the arms 265. In some embodiments, the frame 260 is releasably coupled to the housing of the sensor system 130 via the arms 265.

FIGS. 7-10 illustrate another embodiment of the filter 250'. The filter 250' includes one or more mesh screens 255, the frame 260, and the arms 265. The filter 250' further includes a chimney 270. The chimney 270 is configured to exhaust gas, or air bubbles, entrapped in the measurement channel 205. In some embodiments, the chimney 270 provides an unobstructed path for the gas, or air bubbles, to a location outside the measurement channel 205. In other embodiments, the chimney 270 includes a component designed to allow one-directional flow of a fluid out of the measurement channel 205. In some embodiments, the component is a rubber flap.

In embodiments having a chimney 270, the gas bubbles which collect within the sensing area or sensing areas, i.e. those bubbles which are smaller than the aperture size of the filter screen, are acted upon by the forces of gravity and convection causing the gas bubbles to flow out of the measurement channel 205 through the chimney 270 in the case of the concentration sensor 170, or up the level sensing tube 220 in the case of level sensor 175 (i.e., the level sensing tube 220 acts as an exhaust allowing the trapped gas bubbles to flow upward and out). Once bubbles have exited the sensing areas they are free to escape up through the liquid within the tank to a surface of the fluid.

Figure 11:
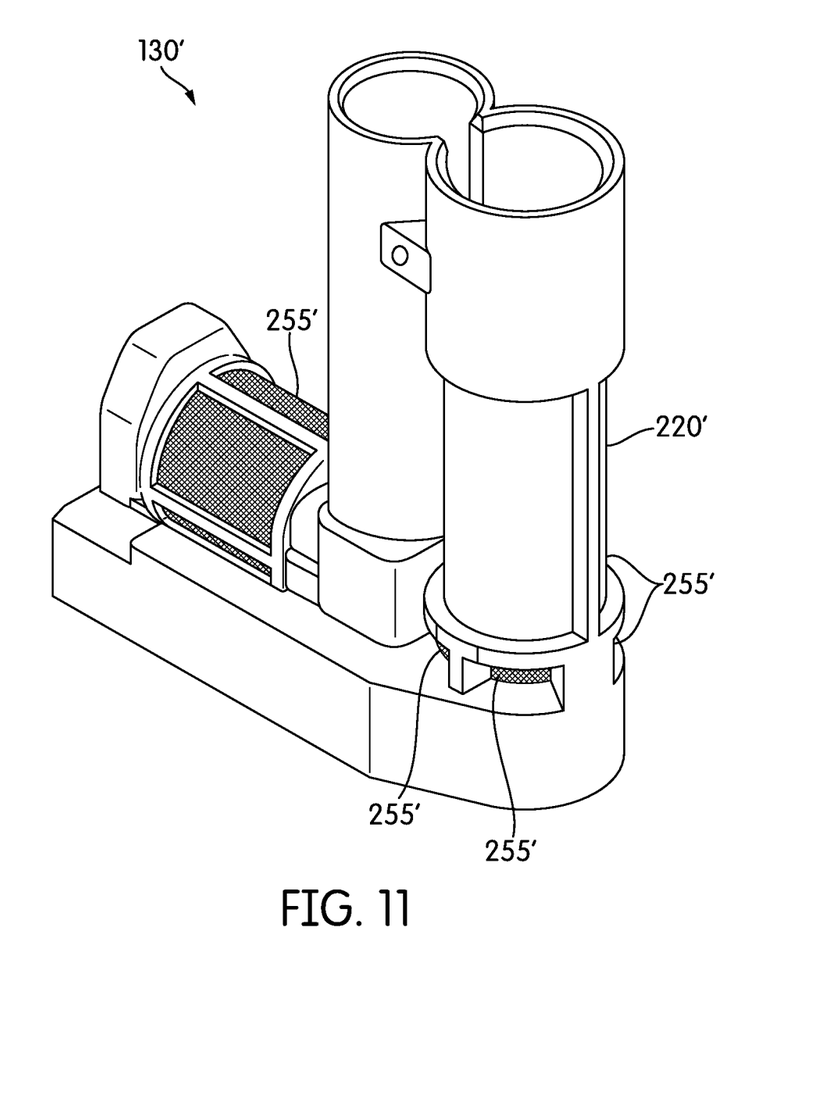
FIG. 11 is a perspective view of another embodiment of a sensing system used in the apparatus of FIG. 1.

FIG. 11 illustrates another embodiment of a sensor system 130'. In the illustrated embodiment, the sensor system 130' includes one or more mesh screens 255'. The mesh screens 255' enclose the sensing areas (e.g., the measurement channel 205, the level sensing tube 220, etc.). In such an embodiment, the filter 250 includes only the mesh screens 255'. In the illustrated embodiment, the mesh screens 255' are integrated (i.e., molded) into a housing of the sensor system 130'.

Figure 12:
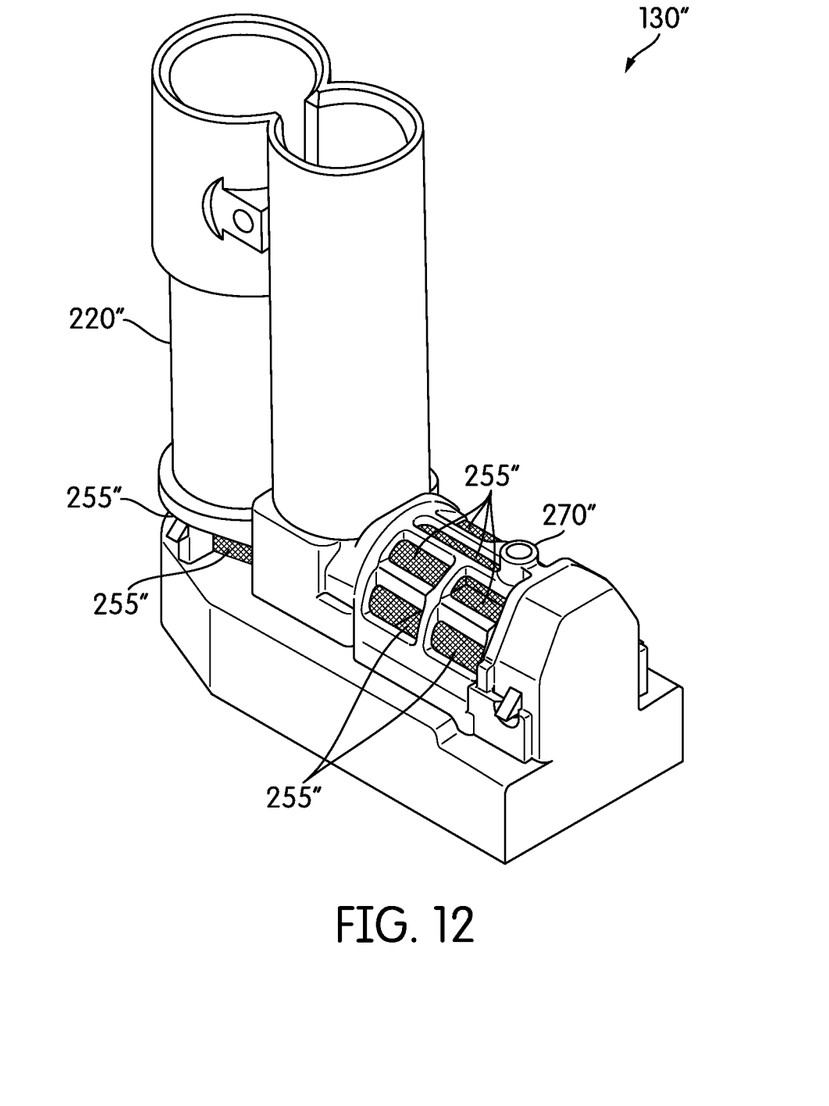
FIG. 12 is a perspective view of another embodiment of a sensing system used in the apparatus of FIG. 1.

FIG. 12 illustrates another embodiment of a sensor system 130". In the illustrated embodiment, the sensor system 130" includes one or more mesh screens 255" enclosing the sensing areas (e.g., the measurement channel 205, the level sensing tube 220, etc.) and a chimney 270". In the illustrated embodiment, the mesh screens 255" and chimney 270" are integrated (i.e., molded) into a housing of the sensor system 130". In such an embodiment, the chimney 270" operates as discussed above in relation to chimney 270.

Thus, the invention provides, among other things, a sensor system including a filter for preventing gas bubbles from entering the sensor system. Various features and advantages of the invention are set forth in the following claims.

What is claimed is:

1. A fluid sensor comprising:
   a housing;
   a sensing area;
   a sensing element configured to sense a characteristic of a fluid located within the sensing area; and
   a mesh enclosing the sensing area, the mesh coupled to the housing via a frame and configured to
      allow a liquid portion of the fluid to enter and exit the sensing area, and
      substantially prohibit one or more gas bubbles of the fluid to enter the sensing area.

2. The fluid sensor of claim 1, wherein the sensing area is one of a measurement channel and a level sensing tube.

3. The fluid sensor of claim 1, wherein substantially prohibiting the one or more gas bubbles of the fluid from entering the sensing area includes dispersing the one or more gas bubbles to produce a homogenous fluid entering the fluid channel.

4. The fluid sensor of claim 1, wherein the sensing element is one of a concentration sensing element, a level sensing element, and a temperature sensing element.

5. The fluid sensor of claim 1, wherein the fluid is one of a urea solution, a gasoline fuel, a diesel fuel, an engine oil, hydraulic fluid, and a transmission fluid.

6. The fluid sensor of claim 1, wherein the housing includes a chimney configured to exhaust entrapped air from the sensing area.

7. The fluid sensor of claim 1, wherein the frame includes two arms, the two arms configured to couple the mesh and frame to the housing.

8. The fluid sensor of claim 7, wherein the frame includes a chimney configured to exhaust entrapped air from the sensing area.

9. A method of preventing gas bubbles in a sensing system for sensing a fluid contained in a tank, the sensing system including a housing, a sensing area and a sensor, the method comprising:
   coupling a mesh to the housing via a frame, wherein the mesh covers the sensing area;
   allowing a liquid portion of the fluid to enter and exit the sensing area through the mesh;
   prohibiting one or more gas bubbles of the fluid entering the sensing area; and
   sensing a characteristic of the fluid contained within the sensing area.

10. The method of claim 9, wherein the sensing area is one of a measurement channel and a level sensing tube.

11. The method of claim 9, wherein prohibiting the one or more gas bubbles of the fluid entering the sensing area includes dispersing the one or more gas bubbles to produce a homogenous fluid entering the fluid channel.

12. The method of claim 9, wherein the sensed characteristic is one of a concentration, a level, and a temperature.

13. The method of claim 9, wherein the fluid is a urea solution, a gasoline fuel, a diesel fuel, an engine oil, hydraulic fluid, and a transmission fluid.

14. The method of claim 9, further comprising exhausting the gas portion of the fluid from the sensing area.

15. The method of claim 9, wherein the frame includes two arms, the two arms configured to couple the mesh and the frame to the housing.

* * * * *